United States Patent [19]
Xiu

[11] Patent Number: 5,616,325
[45] Date of Patent: Apr. 1, 1997

[54] STIMULATOR OF VASCULAR ENDOTHELIAL CELLS AND USE THEREOF

[76] Inventor: Rui J. Xiu, Fatburs Brunnsg., 11 S-118 28 Stockholm, Sweden

[21] Appl. No.: 132,221

[22] Filed: Oct. 6, 1993

Related U.S. Application Data

[63] Continuation of Ser. No. 862,744, filed as PCT/SE90/00868 Dec. 21, 1991, abandoned.

[30] Foreign Application Priority Data

Dec. 22, 1989 [SE] Sweden .................................. 8904353

[51] Int. Cl.$^6$ ..................................................... A61K 35/78
[52] U.S. Cl. ....................... 424/195.1; 514/783; 514/824; 514/929
[58] Field of Search ......................... 424/195.1; 514/885

[56] References Cited

FOREIGN PATENT DOCUMENTS

| 63-83537 | 4/1988 | Japan . |
| 63183537 | 7/1988 | Japan . |

OTHER PUBLICATIONS

Liu Shuhua et al, "Regeneration of hemopoietic tissue in grafted murine femur and demonstration of the effect some radioprotectants," *Chemical Abstracts*, vol. 104, No. 23: p. 380, Abstract No. 203144p, Jun. 9, 1986.

Deng Wenlong et al, "Immunopharmacological study on the polysacharide of tremella(Tremella fuciformis)", *Chemical Abstracts*, vol. 104: p. 37, Abstract No. 122768t, (1986).

Chemical Abst. 104(2.23); 203144p, 1986.

Chemical Abst. 104:122768t, 1986.

Coffin *Science*, vol. 267, pp. 483–489, (1995).

Lawrence *Aids Research and Human Retroviruses*, vol. 10; (12), pp. 1585–1589, (1994).

Press Release –"NIAID Researches Report New Data on Non–Progressive HIV Infection". (25 Jan. 1995).

*Primary Examiner*—Douglas W. Robinson
*Assistant Examiner*—Howard C. Lee
*Attorney, Agent, or Firm*—Browdy and Neimark

[57] ABSTRACT

The use of extracts of *Tremella fuciformis* (Berk) in maintaining the permeability of microvascular walls and its effect on the microcirculatory system, especially with regard to treatment of thromboplebitis, atherosclerosis and senile degradation of microvessels, is described.

10 Claims, 4 Drawing Sheets
(5 of 9 Drawing(s) in Color)

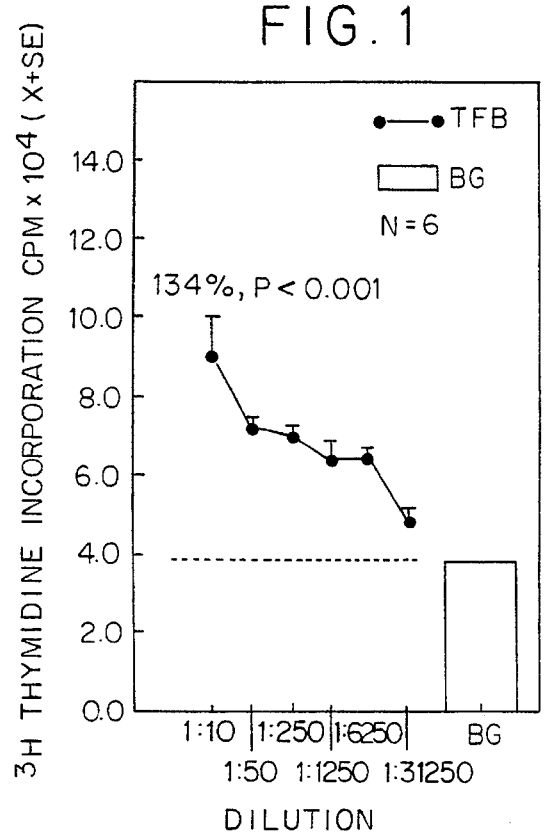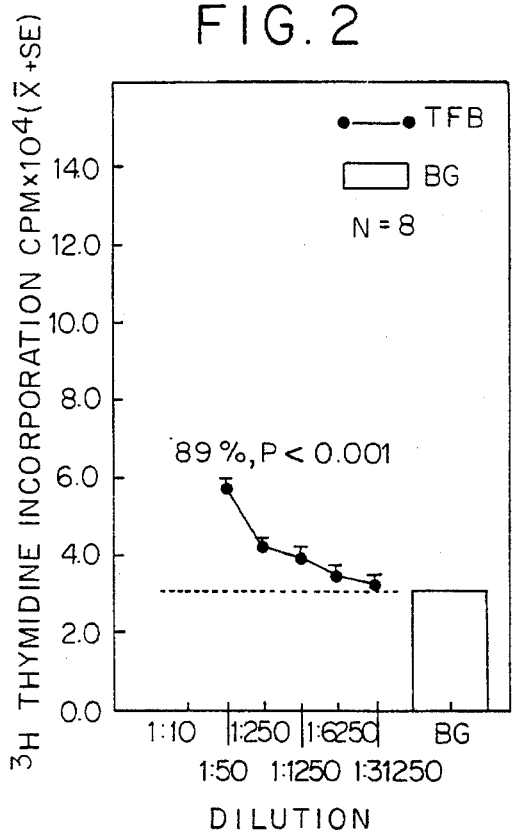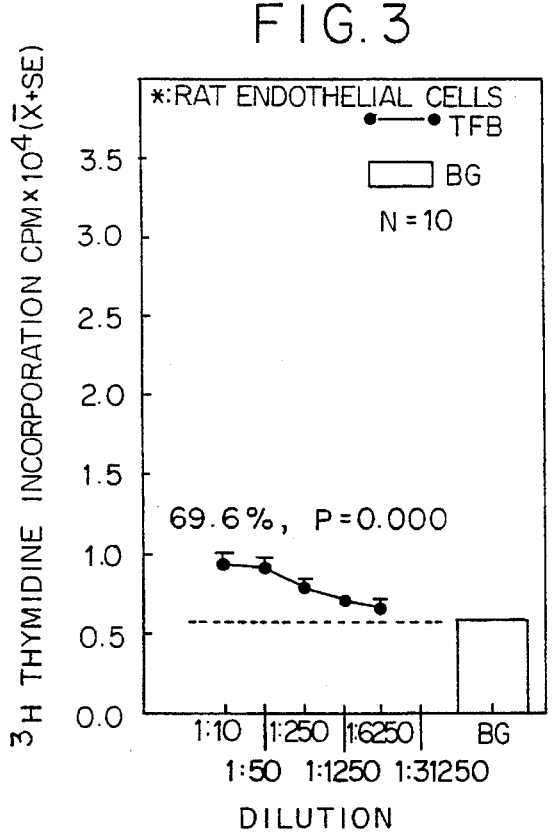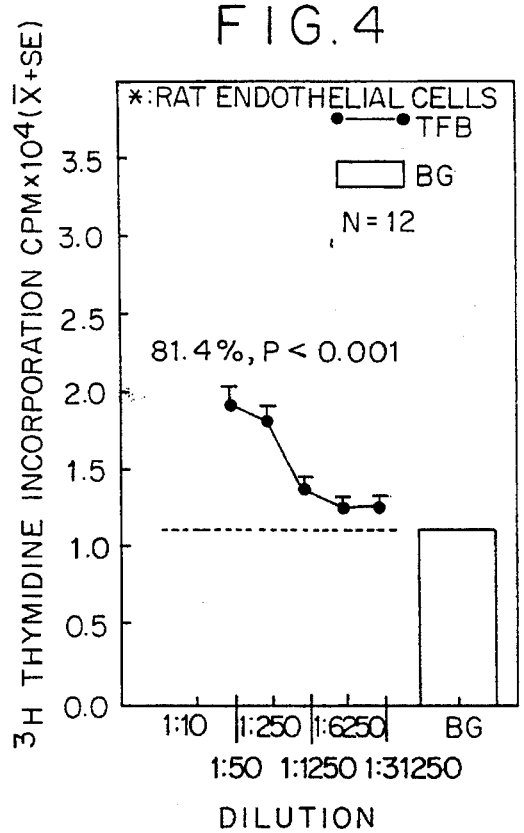

5,616,325

STIMULATOR OF VASCULAR ENDOTHELIAL CELLS AND USE THEREOF

This application is a continuation of application Ser. No. 07/862,744, filed as PCT/SE90/00868 Dec. 21, 1991, now abandoned.

FIELD OF INVENTION

The present invention relates to agents containing extracts of a fungus, *Tremella fuciformis*, Berk (TFB), which is a non-toxic, nutritional remedy, and which agents have a potential stimulating effect on he DNA synthesis of vascular endothelial cells. *Tremella fuciformis*, Berk (TFB) belongs to the class Hymenomycetes, in the division Eumycota (Ainsworth & Bisby's Dictionary of the Fungi, 1971).

BACKGROUND

TFB has long had a good reputation of being a high standard, nutritional remedy in Chinese history. Thus, in ancient medicinal literature TFB has been ascribed certain curative properties, such as: Promoting saliva secretion, moistening lungs and stopping dry cough, decreasing itching in the throat, inhibiting the coughing blood, relieving stomach pain, stopping constipation and blood in the stool, restoring tired muscles, supporting good spirit and memory, keeping skin young end hair shiny etc.

During the last 15–20 years scientific studies of TFB have been carried out in China end Japan- Thus, In Journal of Medicine and Material Medics, 1978, p. 21–25, San Ming Research Station, describe the treatment of chronic bronchitis end chronic pulmonary disease using TFB.

Liu zhi-bin et al reported that, oral or subcutaneous injection of TFB to mice raised the macrophage and enhanced the phagocytic function (Proceeding of Beijing Medical University, 14(1); 14–15, 1982).

Wang Zia-oan et al in Chinese Medical Journal of Radiation end Protection, pp. 65–66, 1983, reported that TFB could prevent the harmful influence of Co-60 irradiation in monkeys by restoring their leucocyte counts back to normal level.

Cheng Zi-qi et al in Chinese Medical Journal of Radiation end Protection, pp 4(3), 54–55, 1984, reported that TFB when given to patients, who had received radiation, or chemotherapy treatment for cancer, raised the B and T lymphocyte count with 8.6% and 11.0% respectively.

Liu shu-hua et al reported (J. Zhonghue Fangshe Yixue Yu Fanghu 5(4), pp. 262–265, 1985), that injection of AET, 5-HT, TFB to donor mice before Co-60 irradiation protected the haemopoietic function of bone marrow. But there was no studies directly towards the effect of TFB on mircovascular endothelial function.

Dang Wen-long et al Immuno-pharmacological study on the polysaccharide of Tremella (Zhongcaoyao 1984, 15(9) 23–6, 22) reported that i.v. injection of *Tremella polysaccharide* (TP) enhanced phagocytotic clearance of C particles and 32P-labeled *Staphylococcus aureus* from the circulation by macrophages of the reticuloendothelial system (RES). It was also found, that TP antagonized the inhibited phagocytotic function of the RES by immune inhibitors. However, there was no disclosure, about the effect of TFB on endothelial cells per se, still less on vascular endothelium, which is different from RES.

Endothelial cells which belong to the reticuloendothelial system (RES) are called "Reticuloendothelial Cells". The name "RES" was proposed 1924 by Dr. Aschoff, who suggested that those mononuclear cells, which possess function of phagocytosis, or of storage some granules and dyes are united as a whole system. These cells have a common defense function in the body, and thus he called these cells: "The Reticuloendothelial System". This system includes fixed or movable macrophages and mononuclear cells in the blood flow. But nowadays this expression has been replaced by "mononuclear phagocytotic system".

Several Japanese patent publications disclose the use of extracts from mycelium end fruit bodies of TFB for antitumor and carcinostatic treatment, cf. the Japanese published patent applications JP57017518-B4; JP6057835-B4; JP54011250-A; JP53107407-A: JP53107406-A.

In 1988, it was reported in JP63183537 that TFB was found to be an anti-inflammatory drug, particularly in the cosmetic field, but there were no experimental and clinical data for showing and proving the anti-inflammatory effect of TFB introduced by this report.

SUMMARY OF THE INVENTION

According to the present invention, it has been found that agents containing extracts of TFB have a stimulating effect on the DNA synthesis of vascular endothelial cells- This effect is of great importance in the microcirculatory system and the fine microvessels therein, for supporting the main life-process, such as growth, development, reproduction and regeneration. These important functions are decreased or inhibited by a ion term suffering from serious diseases, or by natural aging of the body. Thus, an important use of TFB is the treatment of-senile people for preventing senile degeneration of their microvessels in order to keep their brains, hearts and other vital organs in a better condition for improved blood supply.

It has also unexpectedly been found that this stimulating effect on the DNA synthesis of vascular endothelial cells can be used in combination with known HIV-anti-virus agents, such as AZT, in the treatment of AIDS patients to improve their condition. This effect of TFB is directly related with the microcirculatory system since it has been found (example 3) that AIDS patients suffer from microcirculatory disturbances caused by severe damage of vascular endothelial cells, cf. FIGS. 5–9.

BRIEF DESCRIPTION OF DRAWING

The file of this patent contains at least one drawing executed in color. Copies of this patent with color drawing(s) will be provided by the Patent and Trademark Office upon request and payment of the necessary fee.

In the drawings

FIG. 1 shows a curve illustrating the effect of TFB on the DNA synthesis on unconfluented human vascular endothelial cells (5% human serum).

FIG. 2 shows a curve illustrating the effect of TFB on the DNA synthesis of confluented human vascular endothelial cells (5% human Serum).

FIG. 3 shows a curve illustrating the effect of TFB on the DNA synthesis of newborn-rat brain microvessel endothelial cells (REC-unconfluented, 5% FCS).

FIG. 4 shows a curve illustrating the effect of TFB on the DNA synthesis of newborn-rat brain microvessel endothelial cells (REC-unconfluented, 10% FCS)

DETAILED DESCRIPTION OF THE INVENTION

Figure 5:
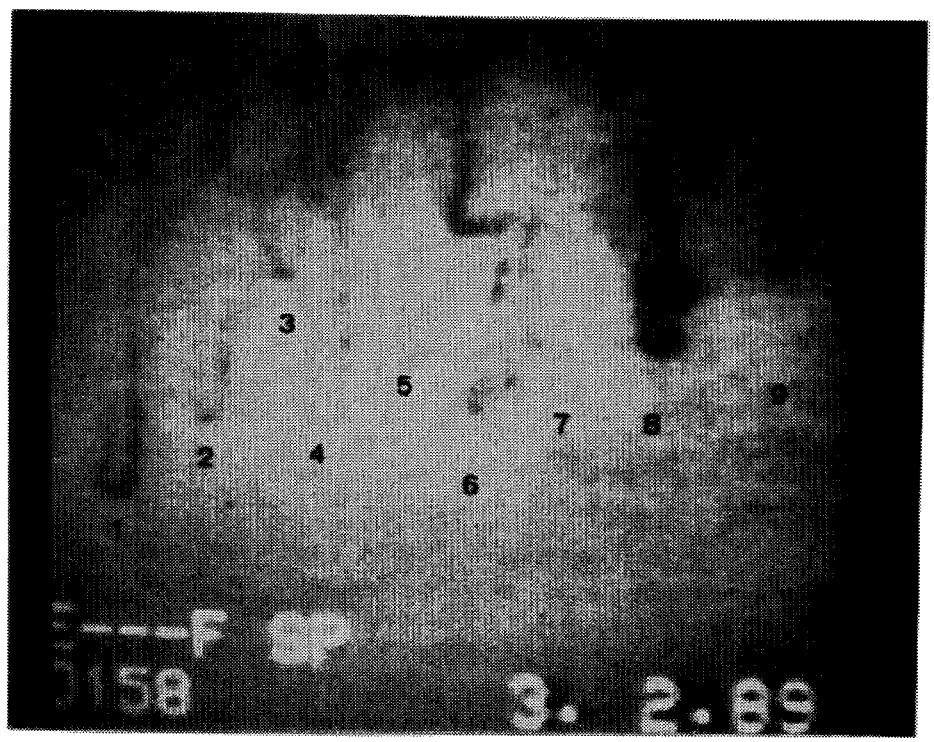
FIG. 5 shows a microphotograph of nail-fold capillary loops (number 1–7) showing poor blood perfusion in an AIDS patient.

Vascular endothelial cells are the endothelium which build up the intimae of the whole cardiovascular system and the lympho-system. These cells are he only matrix of The true capillary wall in the microcirculatory system. Vascular endothelial cells play important roles in the maintenance of physiological homeostasis, and in mediation of micro-vascular response to a variety of physiological, pathological and pharmacological stimulies. Vascular endothelium is the basis of barrier function, such as BBB-the blood brain barrier. Vascular endothelial cells are able to release EDRF (endothelium-derived relaxing factor) and EDCF (endothelium-derived constricting factor) and via these factors to influence the smooth muscle cells, to regulate the vasomotor activities, including he microvascular vasomotion; the disorder of vasomotion plays an important role in ischemic of myocardium and brain. Dysfunction of vascular endothelial cells also is one of the key factor in the pathogenesis of thrombophlebitis, hypertension and atherosclerosis. The vascular endothelial activities are decreased in aging people.

In the experiments described in example 1, it was found that TFB very significantly increased the DNA synthesis of human vascular enothelial cells.

EXAMPLE 1

A. Materials an Methods:
  a. Preparation of TFB stock solution:
  Add 1000 ml bi-distilled water to 10 g dry powder of *Tramella Fuciformis* fruit bodies. Heating on the laboratory electric heater with stir-bar until boiling- Keep boiling or 20 minutes. The suspension is then filtered via 0.22 mm filter (Cambridge, Mass. Cat. No 8110). The received liquor is the TFB stock solution. Frozen at −20° C. The composition:
  (1) Proteins and amino-acids: 15–20%,
  (2) Enzymes: 1–5%
  (3) Polysaccharide: 70–80%.
  b. Preparation of vascular endothelial cells:
  Human vascular endothelial cells (HEC) were isolated from healthy baby umbilical cord vein. The plantation, cultivation and trypsinization of these cells were done according to the standard method.
  c. Assay for DNA synthesis in HEC:

TFB sample in concentration 1:50, 1:250, 1:1250, 1:6250, 1:31250, diluted by M-199+human serum (5% or 10%) was incubated on the 96 flat-bottom plate for 72 hours and then the DNA synthesis was assessed by 24 h 3H-thymidlne pulse (0.5 uci/vell, Boston, USA). The cells were harvested by automatic cell harvester and then counted in new Betaplat liquid Scintillation Counter (LKB1205, Sweden). The data processing was done on a IBM-288 microcomputer.

B. Results:
  a. TFB very significantly increased the DNA synthesis of HEC in a poor nutritional medium (5% human serum); 134% in unconfluented and 89% in confluented condition higher than control group ($p < 0.001$): FIG. 1 and FIG. 2.
  b. TFB quite significantly increased the DNA Synthesis of HEC in a comparatively better nutritional medium (10% human serum); control group ($p < 0.001$).
  c. TBF significantly increased the DNA synthesis of HEC in a good nutritional medium (20% human serum); 32.4% higher than control group ($p < 0.001$) in confluened condition.

In the experiments described in example 2, it was found That TFB has a very significant stimulating effect on the DNA synthesis of brain endothelial cells, which are the cells where the blood brain barrier (BBB) is situated.

EXAMPLE 2

A. Materials and Methods:
  a. TFM stock solution: The same as used in example
  b. Microvascular endothelial cells:
    Isolation of Rat Cerebral Microvessels: In each time of cultivation, 10 new born Wistaer rats were killed via disjointation of cervical vertebra. The whole rat-body was put into 75% ethanol for 2–3seconds. The rat brain were removed via anatomic ally and put into pH 7.4 cold phosphate buffered saline (PBS) (on ice). The 10 brains were cleaned from he pie mater encephali carefully. Then, the brain was rinsed with PBS and homogenized in 10 ml PBS by 20 up and down strokes in a glass homogenizer. The homogenate was filtered over a 88 μm pore nylon sieve and was rinsed with PBS. The collector was rehomogenized in PBS and filtered over a 88 μm sieve again. The microvessel segments were then collected. All the above steps were done under sterile conditions.
    Isolation and Cultivation of RBEC: The cerebral microvessel segments were suspended in 10 ml of PBS containing 10 mg collagenase (Sigma Co., St. Louis) and 10 g bovine serum albumin and then incubated at 37° C. for 10 minutes, centrifuged for 10 minutes at 1000 rpm. The supernatant was discarded and the collagenase-treated microvessels segments were collected and planted to the feeding medium on 60 $m^2$ Petri dishes and hen incubated at 37° C., in 5% $CO_2$ air. After 40 minutes, the medium was changed again with fresh feeding medium containing endothelial cells growth factor. The preparation was repeated every 2–3 days.
    The Medium 199 with 20% fetal calf serum (FCS), 1% glutamine was used as feeding medium. In each ml of feeding medium, 100 μ pencillin, 100 μg streptomycin and 25 μ nystatin were added. The medium was adjusted to pH 7.4 using 2.5% $NaHCO_9$ and filter-sterilized (0.22 μm millipore filter).
    Trypsinization and plantation of RBEC: On the 6–8th day after isolation the RBEC grew on the disks were washed 3 times with PBS and then 0.25% trypsin end 0.02% EDTA was given to each disk. Incubation (37° C.) for 7–8 minutes. The trypsinization was broken by adding 3 ml fresh prepared medium in each disk. Collected all the RBEC together and centrifuged for 5 minutes at 1500 rpm. The supernatant was abandoned. The cells were washed with M-199+20 FCS. The supernatant was abandoned again. Optimal volume of M-199+20% FCS and ECGF was added to the well mixed and using Burker counter counted cells.

Then the cells were planted on 96 wells flat-bottom plate (2500 cells/well) and incubated at 37° C., 5% $CO_2$air, 80% humidity for 24 hours.

c. After 24 hours of plantation the M-199+20% FCS was removed from each well of the 96 wells plate, TFB sample in concentration 1:10, 1:50, 1:250, 1:1250, 1:6250, 1:31250, diluted by M-199+FCS (5% or 10%) was added into the wells according to the prior designed order.

The assay for DNA synthesis in rat brain endothelial cells (RBEC) and the data processing were the same as in example 1.

B. Results:

TFB is very significantly stimulatory to the DNA synthesis of the RBEC:

a. When RBEC were grown with 5% fetal calf serum (FCS) in an unconfluented condition the DNA synthesis was 69.6% greater than control ($p<0.001$). FIG. 3.

b. When RBEC were grown with 10% fetal calf serum (FCS) in unconfluented condition the DNA synthesis was 81.4% higher than control ($p<0.001$). FIG. 4.

EXAMPLE 3

In order to investigate the degree of involvement of vascular perturbations in AIDS patients as a means of developing strategies to help in the treatment of these patients, the Intravital CCTV-microscopic observation of microcirculation in nail-fold was carried out on 11 AIDS patients and 11 healthy European adults. A unique pattern of severe microvascular disturbance was found in these patients, which is seen from FIGS. 5–9 wherein FIG. 5 shows a microphotograph of nail-fold capillary loops (Number 1–7) showing poor blood perfusion that is associated with a dysfunction of automatic alternative capillary flow. Capillary loop #8, 9 end 10 contain a column of slowly moving blood cells that appear aggregated. (Magnification=400).

Figure 6:
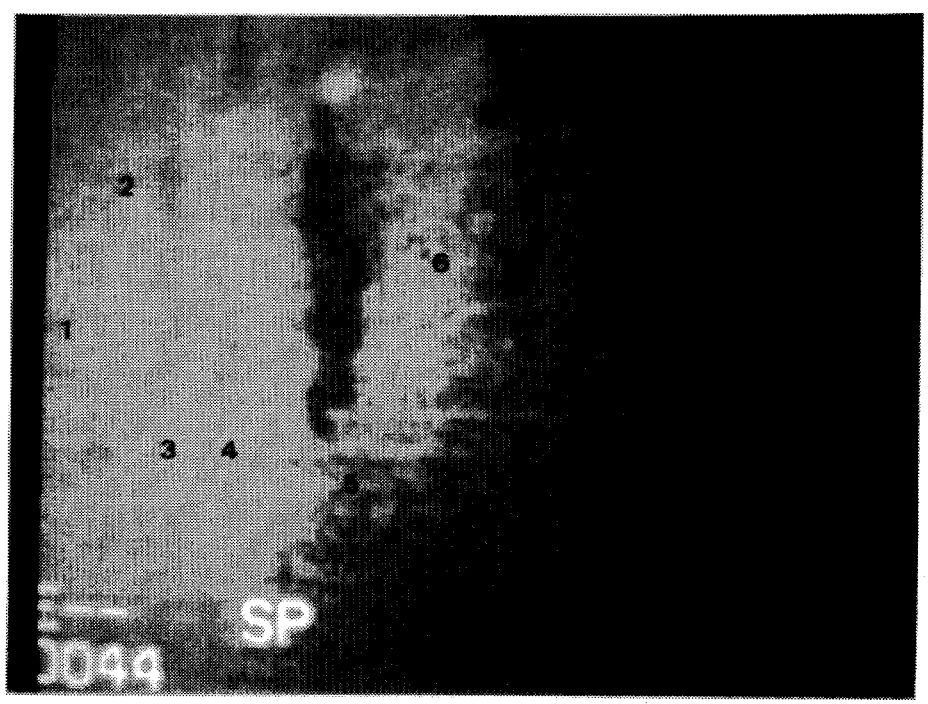
FIG. 6 shows a microphotograph during periods where all of the capillary loops were devoid of active blood flow in an AIDS patient, but the damaged vascular emdothelial cells, the wall of the capillary loop (#5) is still visible in the microscopic field.

FIG. 6 shows a microphotograph during periods where all of the capillary loops were devoid of active blood flow. The damaged wall of the capillary loop (#5) is still visible in the microscopic field. (Magnification=400)

Figure 7:
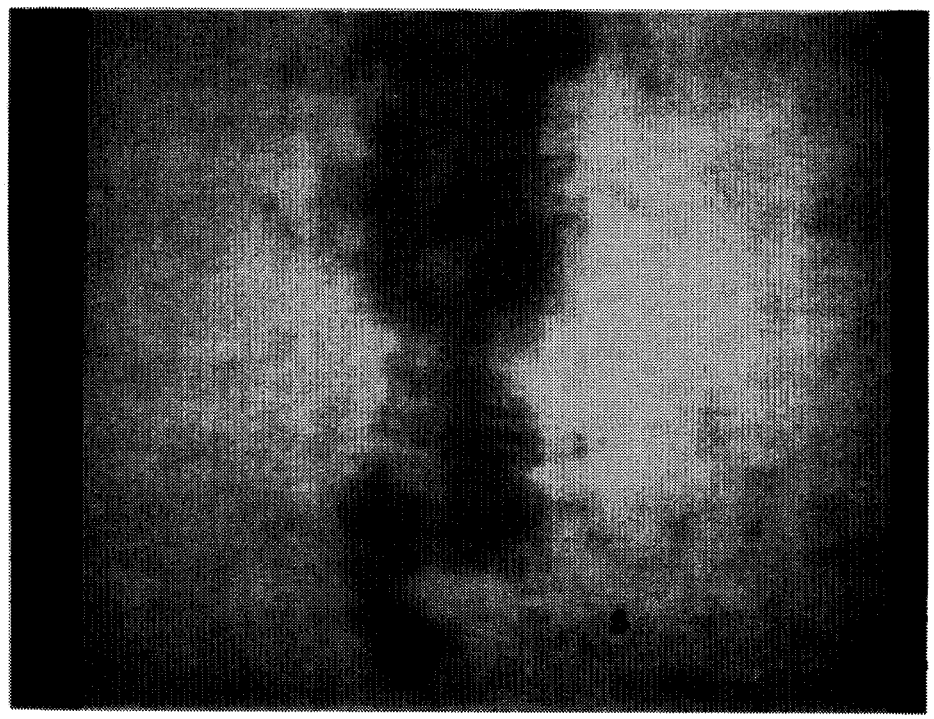
FIG. 7 shows a microphotograph of capillary loop used for computer image analysis of wall (endothelial cells) damage in the nail-fold bed of an AIDS patient.

FIG. 7 shows a microphotograph of vessel loop used for image analysis of wall damage in the nail-fold bed of an AIDS patient. (Magnification=800)

Figure 8:
FIG. 8 shows a microphotograph of nail-fold showing accumulation of red blood cells at the apex region of the capillary loops during periods when the loops were without an active bloodstream in an AIDS patient and FIG. 9 shows a microphotograph illustrating red blood cells extravasated in regions where the capillary loops were leaky (#1, 2, 3, 4) and empty of blood flow in an AIDS patient.

FIG. 8 shows a microphotograph of nail-fold showing accumulation of red blood cells at the apex region of the capillary loops during periods when the loops were without an active bloodstream. (Magnification=400)

Figure 9:
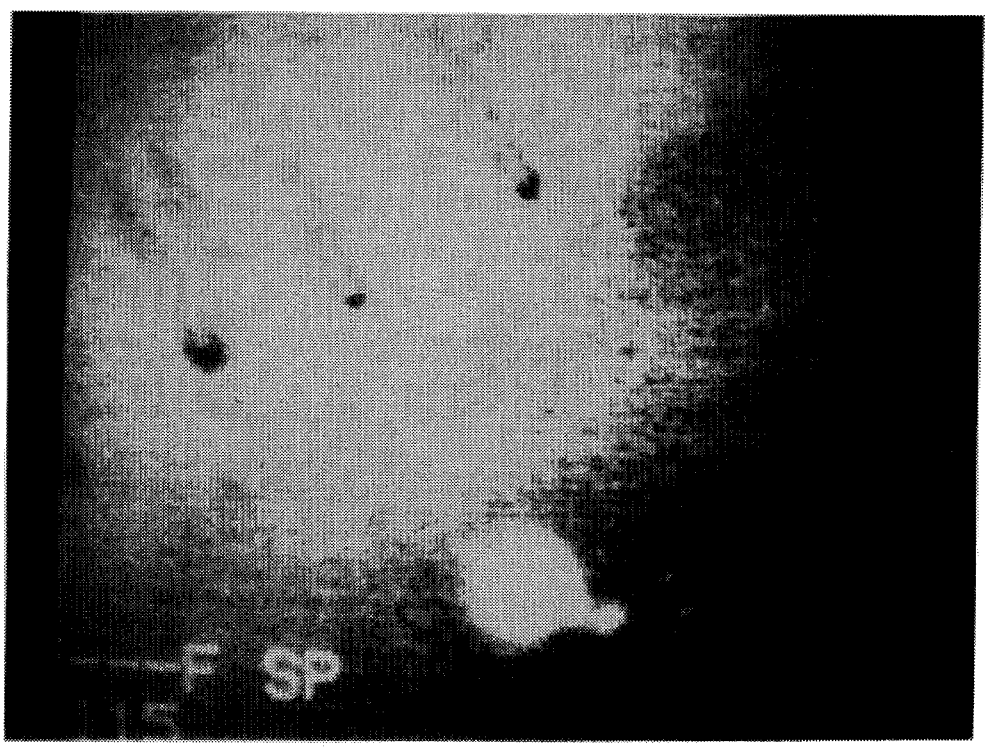

FIG. 9 shows a microphotograph illustrating red blood cells extravasated in regions where the capillary loops were leaky (#1, 2, 3, 4) and empty of blood flow. (Magnification=400)

As seen from these FIGS. 5–9 several severe microvascular disturbances were found in these patients, viz.

1) A suppression of the spontaneous, rhythmic adjustments of capillary blood perfursion (FIG. 5), 2) Remarkable damage to the endothelium of the capillary wall. Computer image analysis of the pathological areas indicates that there are heterogeneous mass in the cytoplasm of the endothelial cells, or around them (FIGS. 6 and 7).

3) Aggregation and extravasation of red cells, low capillary wall tension, high permeability of microvessels wall (FIGS. 8 and 9).

These findings suggest a substantial involvement of the microcirculation in pathogenetic development of AIDS syndrome. In the AIDS clinic, a number of patients exhibited symptoms of microcirculatory dysfunction, such as cold and/or numb extremities, sensory disturbances of the distal extremities which do not conform to a particular nerve distribution, cyanotic, or dusky hands or feet end hairy leukoplkia. The severe impairment of automatic alternative capillary blood flow perfusion, ischemia, hypoxia of the peripheral tissue and widespread damage of microvascular endothelium could explain the above mentioned symptoms.

An AIDS patient (male) in the late stage of AIDS, suffering from Kaposi's sarcoma and with many lesions on the skin over the whole body, was given TFB as a remedy three times a day. After two weeks his general condition had been improved to such an extent that he could leave his bed and stay out of bed all day. The pain around the lesions was much reduced. Furthermore, his appetite was improved to a substantial degree.

EXAMPLE 4

Inhibition of Histamine—induced high permeability of microvascular wall by TFB.

A. Material and Method a. TFB Food for rats: Add 100 ml boiled water to 100 g TFB powder. Steam it in the Chinese cooking steamer for 30 minutes. Save it in the refrigerator for use.

b. Animal: 20 Wistaer rats aged 4 weeks, male.

c. Procedure of experiments:

a) TFB solution was given per os via a injection syringe with a long dull needle, 2 times a day, 1 ml/time, to the 10 rats of the experimental group, end the boiled pure water was given to another 10 rats of the control group vie the same way for 7 days.

b) Operation for Isolation of cremaster was done under anesthesia with pentobarbital (50 mg/kg). Then the cremaster was suspended in a Krebs bath ($PCO_2$=40 mm Hg, $PO_2$=34.5 mm Hg, pH=7.4, temp.=34.5° C.). Fluorescein isothiocyanete (FITC) labeled albumin was injected via arterie femoralis. The fluorescent intensity of the micro-circulation was measured on he recorded computer image under the fluorescent television microscopy.

B. Results:

a. Histamine (added in the bath) caused a concentration dependen leakage of the FITC-labeled albumin from the microvessels in the rats of control group.

b. The leakage of FITC-labeled albumin was significantly inhibited ($P<0.01$) in the microvessels of the TFB feedad rats (experimental group).

c. Before addition of histamine to the Krebs bath, leakage of the FITC-labeled albumin from the microvessels did not occur in any group of rats.

The use of extracts of Tremella fuciforms (Berk) in maintaining the permeability of microvascular walls and its effect on the microcirculatory system, especially with regard to treatment of thromboplebitis, atherosclerosis and senile degradation of microvessels, is described.

TABLE 1

Effect of TBF on High Permeability Induced by Histamine

| Group | Before Histamine | Concentration of Histamine (molar) | | | |
|---|---|---|---|---|---|
| | | $1 \times 10^{-6}$ | $1 \times 10^{-5}$ | $1 \times 10^{-4}$ | $1 \times 10^{-3}$ |
| Control | 9 ± 1.1 | 9 ± 1.2 | 12 ± 1.1 | 32 ± 3.2 | 61 ± 4.5 |
| Experimental | 9 ± 0.9 | 9 ± 0.5 | 11 ± 3.4 | *14 ± 2.6 | *18 ± 5.1 |

*P < 0.01

The permeability of microvascular wall to a large extent is dependent on the condition of interendothelial cell functions. The results of this experiment showed that it is possible, that the endothelial gap formation in microvascular wall was potentiated by histamine and this was the reason for the macromolecular protein leakage from the microvessels. Our findings indicate hat TFB could protect the vascular endothelial cells against the histamine damage.

Activation of DNA synthesis in the endothelial cells by TFB should be an important part of the mechanism in maintenance of optimal permeability of microvascular wall. This effect of TFB is extremely important in AIDS patients for defending their microcirculatory function, particularly at the early stage of this disease.

I claim:

1. A method for treating an individual with a disease which disturbs microcirculation comprising maintaining the permeability of the microvascular wall in the individual by administering a therapeutically effective amount of an aqueous extract of Tremella fuciformis (Berk) to the individual.

2. A method according to claim 1, wherein said individual is a human.

3. A method according to claim 1, wherein said aqueous extract is prepared by boiling the fruit bodies of Tremella fuciformis (Berk).

4. A method according to claim 1, wherein said aqueous extract is administered orally.

5. A method according to claim 1, wherein said disease is thrombophlebitis.

6. A method according to claim 1, wherein said disease is atherosclerosis.

7. A method according to claim 1, wherein said disease results in a senile degradation of microvessels in the brain.

8. A method of therapy for protecting vascular endothelial cells against histamine damage in a patient in need of said therapy, comprising administering a therapeutically effective amount of an aqueous extract of Tremella fuciformis (Berk) to said patient.

9. A method according to claim 8, wherein said patient is one suffering from natural aging.

10. A method according to claim 8, wherein said aqueous extract comprises a diluted Tremella fuciformis (Berk) stock solution obtained by boiling a dry powder of Tremella fuciformis fruit bodies in water and filtering off the solids, said stock solution comprising on a dry basis 15–20% proteins and amino acids, 1–5% enzymes and 70–80% polysaccharide.

* * * * *